(12) United States Patent
Hitzel et al.

(10) Patent No.: US 7,311,895 B2
(45) Date of Patent: Dec. 25, 2007

(54) COSMETIC FORMULATION COMPRISING DIHYDROXYACETONE

(75) Inventors: Sabine Hitzel, Darmstadt (DE); Hans-Jürgen Driller, Groβ-Umstadt (DE)

(73) Assignee: Merck Patentgesellschaft Mit Beschrankter Haftung, Darmstadt (DE)

( * ) Notice: Subject to any disclaimer, the term of this patent is extended or adjusted under 35 U.S.C. 154(b) by 811 days.

(21) Appl. No.: 10/485,389

(22) PCT Filed: Jul. 5, 2002

(86) PCT No.: PCT/EP02/07522

§ 371 (c)(1),
(2), (4) Date: Jan. 30, 2004

(87) PCT Pub. No.: WO03/011240

PCT Pub. Date: Feb. 13, 2003

(65) Prior Publication Data

US 2004/0185072 A1    Sep. 23, 2004

(30) Foreign Application Priority Data

Jul. 31, 2001   (DE) .................. 101 37 260

(51) Int. Cl.
*A61Q 17/04*   (2006.01)
*A61Q 19/04*   (2006.01)
*A61K 8/02*    (2006.01)

(52) U.S. Cl. .................. 424/59; 424/60; 424/400; 424/401

(58) Field of Classification Search ............ 424/59, 424/60, 400, 401
See application file for complete search history.

(56) References Cited

U.S. PATENT DOCUMENTS 5,705,145 A   1/1998   Miklean et al.

FOREIGN PATENT DOCUMENTS

| DE | 195 05 154 | 8/1996 |
|---|---|---|
| DE | 199 33 466 | 1/2000 |
| DE | 198 34 816 | 2/2000 |
| FR | 2 779 958 | 12/1999 |
| WO | 94 23693 | 10/1994 |

OTHER PUBLICATIONS

M. Eisvogel, "Sun Protection with Anti-Ageing Merck Puts Ectoin to Work", *Cossma: Cosmetics, Spray Technology, Marketing*, Braun Fachverlage, Karlsruhe, DE, Bd. 2, Nr. 4 (Apr. 2001).

*Primary Examiner*—Shelley A. Dodson
(74) *Attorney, Agent, or Firm*—Millen, White, Zelano & Branigan, P.C.

(57) ABSTRACT

The invention relates to cosmetic formulations containing dihydroxy-acetone and a topical support in addition to one or several compounds selected from the compounds of formulae (Ia) and (Ib), the physiologically acceptable salts of compounds of formulae (Ia) and (Ib), and the stereoisomeric forms of formulae (Ia) and (Ib), wherein $R^1$, $R^2$, $R^3$, $R^4$ and n have the meanings cited in Claim 1. The cosmetic formulations are characterized in that the UV-A protective effect of dihydroxyacetone is increased.

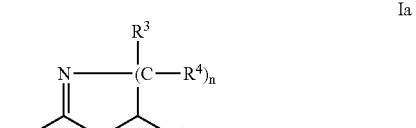

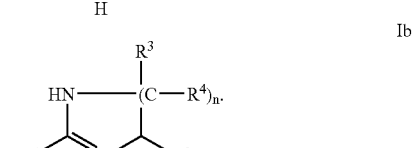

10 Claims, No Drawings

COSMETIC FORMULATION COMPRISING DIHYDROXYACETONE

The invention relates to cosmetic formulations based on dihydroxyacetone. These formulations can be used, for example, for self-tanning.

A certain degree of tanning of the skin is regarded in modern society as attractive and as an expression of vigour and sportiness. Tanning of this type can be achieved, for example, by means of sunbathing or through the use of self-tanning agents.

In addition to the desired action of the sun, tanning, a number of undesired side effects, such as sunburn or premature skin ageing and wrinkling, also occur on exposure of the human skin to the sun. As is known, the most dangerous part of sunlight is formed by ultraviolet rays having a wave-length of less than 400 nm. Part of this UV radiation, UV-A radiation in the range from 320 to 400 nm, tans the skin, but also causes it to age and promotes the initiation of erythematic reactions. It may also increase the erythematic reaction in certain people or even initiate phototoxic or photoallergic and irritative reactions.

However, the tanning achieved through exposure of the human skin to the sun also forms a certain degree of natural protection of the skin against UV rays, i.e. people who already have tanned skin through exposure to the sun are better protected, for example, against the harmful effects of UV-A radiation than are people whose skin has not yet been tanned by exposure to the sun.

It is known, for example, that compounds containing a ketol group

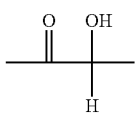

such as, for example, hydroxymethyl ketones, for example methylglyoxal and in particular dihydroxyacetone, exert a self-tanning action on the human skin and are therefore suitable for use in self-tanning agents. The self-tanning effect of these compounds is essentially based on a Maillard reaction between the ketol group of these compounds and the amino acids of the skin.

There are, for example, also indications that the tanning of the skin caused by dihydroxyacetone likewise provides protection against UV-A rays [K. A. Follett et al., Dermatologica 175 (1987) 58-63; J. A. Johnson et al., Dermatologica 175 (1987) 53-57; R. A. Wakeel et al., British Journal of Dermatology 1 (1992) 94]. However, this protection is comparatively weak. It is generally known that the protection against UV-A rays achieved through tanning of the skin achieved with the aid of dihydroxyacetone is not as pronounced as the protection effected by sun tanning. The user of self-tanning compositions based on dihydroxyacetone should accordingly make particularly sure that their skin is protected against UV and in particular against UV-A rays if they are exposed to these rays.

The object of the present invention was therefore to provide cosmetic formulations based on dihydroxyacetone which avoid the disadvantages of the prior art and in particular result in improved UV-A protection when applied to the skin.

Surprisingly, it has now been found that this object is achieved through the use of one or more compounds selected from the compounds of the formulae Ia and Ib

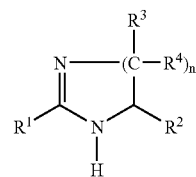

Ia

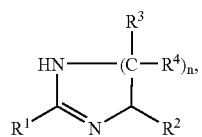

Ib physiologically tolerated salts of the compounds of the formulae Ia and Ib and stereoisomeric forms of the compounds of the formulae Ia and Ib, where $R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having from 1 to 4 carbon atoms, and
$R^5$ is H, alkyl, an amino acid radical, a dipeptide radical or a tripeptide radical, in cosmetic formulations comprising dihydroxyacetone and a topical vehicle.

The invention thus relates to cosmetic formulations comprising dihydroxy-acetone and a topical vehicle, characterised in that the composition additionally comprises one or more compounds selected from the compounds of the formulae Ia and Ib

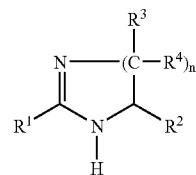

Ia

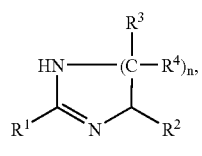

Ib physiologically tolerated salts of the compounds of the formulae Ia and Ib and stereoisomeric forms of the compounds of the formulae Ia and Ib, where $R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having from 1 to 4 carbon atoms, and
$R^5$ is H, alkyl, an amino acid radical, a dipeptide radical or a tripeptide radical.

It is also surprising that the formulations comprising dihydroxyacetone and one or more compounds selected from the compounds of the formulae Ia and Ib, physiologically tolerated salts of the compounds of the formulae Ia and Ib and stereoisomeric forms of the compounds of the formulae Ia and Ib are stable since it is generally known that formulations comprising dihydroxyacetone and nitrogen-containing compounds, such as, for example, amino acids, have stability problems. This is attributable, for example, to the degradation of dihydroxyacetone in the presence of amino acids, which is even accelerated at elevated temperature. However, it has been found that dihydroxyacetone and one or more compounds selected from the compounds of the formulae Ia and Ib, physiologically tolerated salts of the compounds of the formulae Ia and Ib and stereoisomeric forms of the compounds of the formulae Ia and Ib can be incorporated into cosmetic formulations without stability problems arising or particular precautions having to be taken with respect to the stability of the resultant cosmetic formulation. This also applies, for example, within a certain latitude for an elevated storage temperature of the cosmetic formulations according to the invention.

For the purposes of the present invention, all compounds above and below selected from the compounds of the formulae Ia and Ib, physiologically tolerated salts of the compounds of the formulae Ia and Ib and stereoisomeric forms of the compounds of the formulae Ia and Ib are referred to as "ectoin or ectoin derivatives".

Ectoin and ectoin derivatives are low-molecular-weight, cyclic amino acid derivatives which can be isolated from various halophilic microorganisms or prepared synthetically. Both ectoin and hydroxyectoin have the advantage of not reacting with the cell metabolism.

The compounds selected from the compounds of the formulae Ia and Ib, physiologically tolerated salts of the compounds of the formulae Ia and Ib and stereoisomeric forms of the compounds of the formulae Ia and Ib may be present in the cosmetic formulations according to the invention in the form of optical isomers, diastereomers, racemates, zwitterions, cations or a mixture thereof. Of the compounds selected from the compounds of the formulae Ia and Ib, physiologically tolerated salts of the compounds of the formulae Ia and Ib and stereoisomeric forms of the compounds of the formulae Ia and Ib, preference is given to those compounds in which $R^1$ is H or $CH_3$, $R^2$ is H or COOH, $R^3$ and $R^4$ are each, independently of one another, H or OH, and n is 2. Of the compounds selected from the compounds of the formulae Ia and Ib, physiologically tolerated salts of the compounds of the formulae Ia and Ib and stereoisomeric forms of the compounds of the formulae Ia and Ib, particular preference is given to the compounds (S)-1,4,5,6-tetrahydro-2-methyl-4-pyrimidinecarboxylic acid (ectoin) and (S,S)-1,4,5,6-tetrahydro-5-hydroxy-2-methyl-4-pyrimidine-carboxylic acid (hydroxyectoin).

The amino acid radicals mentioned in the radical $R^5$ of the compounds of the formulae Ia and Ib are derived from the corresponding amino acids. The term "amino acids" is taken to mean the stereoisomeric forms, for example D and L forms, of the following compounds: alanine, β-alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, γ-aminobutyrate, Nε-acetyllysine, Nδ-acetylornithine, Nγ-acetyldiaminobutyrate and Nα-acetyldiaminobutyrate. L-amino acids are preferred. The radicals of the following amino acids are preferred: alanine, β-alanine, asparagine, aspartic acid, glutamine, glutamic acid, glycine, serine, threonine, valine, γ-aminobutyrate, Nε-acetyllysine, Nδ-acetylornithine, Nγ-acetyldiaminobutyrate and Nα-acetyldiaminobutyrate.

The di- and tripeptide radicals mentioned in the radical $R^5$ of the compounds of the formulae Ia and Ib are acid amides from the point of view of their chemical nature and decompose on hydrolysis to give 2 or 3 amino acids. The amino acids in the di- and tripeptide radicals are bonded to one another by amide bonds. Preferred di- and tripeptide radicals are built up from the preferred amino acids.

The alkyl groups mentioned in the radicals $R^1$, $R^2$ and $R^5$ of the compounds of the formulae Ia and Ib include the methyl group $CH_3$, the ethyl group $C_2H_5$, the propyl groups $CH_2CH_2CH_3$ and $CH(CH_3)_2$ and the butyl groups $CH_2CH_2CH_2CH_3$, $H_3CCHCH_2CH_3$, $CH_2CH(CH_3)_2$ and $C(CH_3)_3$. The preferred alkyl group is the methyl group.

Preferred physiologically tolerated salts of the compounds of the formulae Ia and Ib are, for example, alkali metal, alkaline earth metal or ammonium salts, such as Na, K, Mg or Ca salts, and salts derived from the organic bases triethylamine or tris(2-hydroxyethyl)amine. Further preferred physiologically tolerated salts of the compounds of the formulae Ia and Ib are formed by reaction with inorganic acids, such as hydrochloric acid, sulfuric acid and phosphoric acid, or with organic carboxylic or sulfonic acids, such as acetic acid, citric acid, benzoic acid, maleic acid, fumaric acid, tartaric acid and p-toluenesulfonic acid.

Compounds of the formulae Ia and Ib in which basic and acidic groups, such as carboxyl or amino groups, are present in the same number form internal salts.

The preparation of the compounds of the formulae Ia and Ib is described in the literature (DE 43 42 560). (S)-1,4,5,6-tetrahydro-2-methyl-4-pyrimidinecarboxylic acid and (S,S)-1,4,5,6-tetrahydro-5-hydroxy-2-methyl-4-pyrimidinecarboxylic acid can also be obtained microbiologically (Severin et al., J. Gen. Microb. 138 (1992) 1629-1638).

The use of compounds selected from the compounds of the formulae Ia and Ib for cosmetic and also pharmaceutical purposes is already known.

For example, WO 94/15923 describes that (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid can be used for the preparation of a cosmetic preparation or of a medicament, for example for the treatment of skin diseases.

Furthermore, DE 43 42 560 describes the use of ectoin and ectoin derivatives as moisturisers in cosmetic products. These products are suitable, for example, for the care of aged, dry or irritated skin.

DE 199 33 466 furthermore describes that ectoin and derivatives, such as hydroxyectoin, can be employed as antioxidants and free-radical scavengers in cosmetic and dermatological preparations. The preparations can be used for the treatment and/or prophylaxis of skin ageing caused by oxidative stress and of inflammatory reactions.

Further applications of ectoin and ectoin derivatives in cosmetic formulations are described, for example, in WO 00/07558, WO 00/07559 and WO 00/07560, such as, for example, the care and prophylaxis of dry and/or flaky skin, protection of human skin against dryness and/or high salt concentrations, protection of cells, proteins and/or biomembranes of human skin, protection of the microflora of human skin, stabilisation of the skin barrier, and protection and stabilisation of the nucleic acids of human skin cells.

However, it was hitherto not known that the compounds selected from the compounds of the formulae Ia and Ib can advantageously be used in cosmetic formulations comprising dihydroxyacetone and that they can significantly augment, for example, the UV-A-protective action of dihydroxyacetone.

The present invention therefore also relates to the use of one or more compounds selected from the compounds of the formulae Ia and Ib for augmenting the UV-A-protective action of dihydroxyacetone, in particular in cosmetic formulations.

However, the cosmetic formulations according to the invention are also suitable, for example, for the applications of ectoin and derivatives thereof which are mentioned above and those which are known from the prior art. The present application therefore likewise relates to the use of the cosmetic formulations according to the invention for these applications.

Examples of the cosmetic formulations according to the invention are, inter alia, self-tanning compositions, products for day care and light-protection formulations. In a preferred embodiment, the cosmetic compositions according to the invention are used as self-tanning agents.

The proportion of dihydroxyacetone in the cosmetic formulation according to the invention is preferably from 0.1 to 15% by weight, particularly preferably from 0.1 to 10% by weight and especially preferably from 1 to 7% by weight, based on the formulation as a whole. The proportion of dihydroxyacetone in the cosmetic formulation according to the invention is very especially preferably from 2 to 5% by weight, based on the formulation as a whole.

The proportion of compounds selected from the compounds of the formulae Ia and Ib, physiologically tolerated salts of the compounds of the formulae Ia and Ib and stereoisomeric forms of the compounds of the formulae Ia and Ib in the cosmetic formulation according to the invention is preferably from 0.001 to 50% by weight, particularly preferably from 0.01 to 10% by weight and especially preferably from 0.1 to 10% by weight, based on the cosmetic formulation as a whole. The proportion of the said compounds in the cosmetic formulation according to the invention is very especially preferably from 0.1 to 5% by weight, based on the formulation as a whole.

Besides dihydroxyacetone and the compounds of the formula I, the cosmetic formulations according to the invention may also comprise further cosmetic active ingredients.

The cosmetic formulations according to the invention may comprise one or more antioxidants. The cosmetic formulations according to the invention may comprise all common antioxidants. In this connection, there are many proven substances known from the specialist literature which can be used as antioxidants, for example flavonoids, coumaranones, amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and hepta-thionine sulfoximine) in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxy-anisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide), metal bisulfite salts, sulfite salts or hydrogensulfite salts.

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

A further suitable antioxidant mixture can consist, for example, of, inter alia, emblicanin A, emblicanin B, punigluconin and pendunculagin, as described, for example, in WO 00/48551 under the name CAPROS™ (for example Emblica™).

In a preferred embodiment of the invention, the cosmetic formulation according to the invention comprises one or more compounds selected from flavonoids and/or coumaranones.

Flavonoids are taken to mean the glycosides of flavonones, flavones, 3-hydroxyflavones (=flavonols), aurones, isoflavones and rotenoids [Römpp Chemie Lexikon [Römpp's Lexicon of Chemistry], Volume 9, 1993]. For the purposes of the present invention, however, this term is also taken to mean the aglycones, i.e. the sugar-free constituents, and the derivatives of the flavonoids and aglycones. For the purposes of the present invention, the term flavonoid is furthermore also taken to mean anthocyanidine (cyanidine). For the purposes of the present invention, the term coumaranones is also taken to mean the derivatives thereof.

Preferred flavonoids are derived from flavonones, flavones, 3-hydroxy-flavones, aurones and isoflavones, in particular from flavonones, flavones, 3-hydroxyflavones and aurones.

The flavonoids are preferably selected from the following compounds: 4,6,3',4'-tetrahydroxyaurone, quercetin, rutin, isoquercetin, eriodictyol, taxifolin, luteolin, trishydroxyethylquercetin (troxequercetin), trishydroxyethylrutin (troxerutin), trishydroxyethylisoquercetin (troxeisoquercetin), trishydroxyethylluteolin (troxeluteolin), α-glycosylrutin, tiliroside and the sulfates and phosphates thereof. Of the flavonoids, particular preference is given to rutin and troxerutin.

Of the coumaranones, preference is given to 4,6,3',4'-tetrahydroxybenzyl-3-coumaranone.

In a further preferred embodiment of the invention, in particular if the water solubility of the flavonoids and/or coumaranones is to be increased, a polar group, for example, in each case independently of one another, a sulfate or phosphate group, is bonded to one or more hydroxyl groups of these compounds. Suitable counterions are, for example, the ions of the alkali or alkaline earth metals, these being selected, for example, from sodium and potassium.

Many flavonoids and coumaranones are, for example, naturally occurring. If the cosmetic formulation according to the invention comprises such compounds, they may also be obtained by extraction of corresponding plants and either purified as a single substance or alternatively introduced into the cosmetic formulation in the form of the extract, which may, if necessary, have been refined further.

The proportion of the one or more compounds selected from flavonoids and coumaranones in the cosmetic formulation according to the invention is preferably from 0.001 to 5% by weight, particularly preferably from 0.01 to 2% by weight, based on the formulation as a whole.

In a further preferred embodiment of the invention, the cosmetic formulation according to the invention comprises one or more antioxidants selected from the substances citric acid, lactic acid, malic acid, EDTA, butylhydroxytoluene, ascorbic acid, ascorbyl palmitate, magnesium ascorbyl phosphate, ascorbyl acetate, tocopherol, tocopherol acetate, and metabisulfite, sulfite or hydrogensulfite salts selected from alkali metal salts, such as sodium and potassium salts, basic metal salts and ammonium salts.

In a further preferred embodiment of the invention, the cosmetic formulation according to the invention comprises antioxidant mixtures, such as, for example, Emblica™.

The proportion of the one or more antioxidants in the cosmetic formulation according to the invention is preferably from 0.001 to 5% by weight, particularly preferably from 0.01 to 2% by weight, based on the formulation as a whole.

The cosmetic formulations according to the invention may comprise one or more UV filters. Suitable organic UV filters are all UVA and UVB filters known to the person skilled in the art. For both UV ranges, there are many proven substances which are known from the specialist literature, for example benzylidenecamphor derivatives, such as
    3-(4'-methylbenzylidene)-dl-camphor (for example Eusolex® 6300),
    3-benzylidenecamphor (for example Mexoryl® SD),
    polymers of N-{(2 and 4)-[(2-oxoborn-3-ylidene)methyl]benzyl}acrylamide (CAS No. 113783-61-2, for example Mexoryl® SW),
    N,N,N-trimethyl-4-(2-oxoborn-3-ylidenemethyl)anilinium methylsulfate (CAS No. 52793-97-2, for example Mexoryl® SK) or
    α-(2-oxoborn-3-ylidene)toluene-4-sulfonic acid (CAS No. 56039-58-8, for example Mexoryl® SL),
benzoyl- or dibenzoylmethanes, such as
    1-(4-tert-butylphenyl)-3-(4-methoxyphenyl)propane-1,3-dione (for example Eusolex® 9020) or
    4-isopropyidibenzoylmethane (for example Eusolex® 8020),
benzophenones, such as
    2-hydroxy-4-methoxybenzophenone (for example Eusolex® 4360) or
    2-hydroxy-4-methoxybenzophenone-5-sulfonic acid and its sodium salt (for example Uvinul® MS-40),
methoxycinnamic acid esters, such as
    octyl methoxycinnamate (for example Eusolex® 2292),
    isopentyl 4-methoxycinnamate, for example as a mixture of the isomers (for example Neo Heliopan® E 1000),
salicylate derivatives, such as
    2-ethylhexyl salicylate (for example Eusolex® OS),
    4-isopropylbenzyl salicylate (for example Megasol®) or
    3,3,5-trimethylcyclohexyl salicylate (for example Eusolex® HMS),
4-aminobenzoic acid and derivatives, such as
    4-aminobenzoic acid,
    2-ethylhexyl 4-(dimethylamino)benzoate (for example Eusolex® 6007),
    ethoxylated ethyl 4-aminobenzoate (for example Uvinul® P25),
benzimidazole derivatives, such as
    2-phenylbenzimidazole-5-sulfonic acid and potassium, sodium and triethanolamine salts thereof (for example Eusolex® 232),
    2,2'-(1,4-phenylene)bis(1H-benzimidazole-4,6-disulfonic acid, mono-sodium salt) (CAS No. 180 898-37-7, for example Neo Heliopan AP),
    2,2'-(1,4-phenylene)bis(1H-benzimidazole-5-sulfonic acid) and potassium, sodium and triethanolamine salts thereof,
and further substances, such as
    2-ethylhexyl 2-cyano-3,3-diphenylacrylate (for example Eusolex® OCR),
    3,3'-(1,4-phenylenedimethylene)bis(7,7-dimethyl-2-oxo-bicyclo[2.2. 1]-hept-1-ylmethanesulfonic acid and salts thereof (for example Mexoryl® SX),
    2,4,6-trianilino-(p-carbo-2'-ethylhexyl-1'-oxy)-1,3,5-triazine (for example Uvinul® T 150),
    2-(2H-benzotriazol-2-yl)-4-methyl-6-(2-methyl-3-(1,3,3,3-tetramethyl- 1-(trimethylsilyloxy)disiloxanyl)propyl)phenol (for example Silatrizole®),
    2-ethylhexyl 4,4'-[(6-[4-((1,1-dimethylethyl)aminocarbonyl)phenyl-amino]-1,3,5-triazine-2,4-diyl)diimino]bis (benzoate) (CAS NO. 154702-15-5, for example Uvasorb® HEB),
    α-(trimethylsilyl)-ω-[trimethylsilyl)oxy]poly[oxy(dimethyl [and about 6% of methyl[2-[p-[2,2-bis(ethoxycarbonyl]vinyl]phenoxy]-1-methyleneethyl] and about 1.5% of methyl[3-[p-[2,2-bis(ethoxycarbonyl)vinyl)phenoxy)-propenyl) and from 0.1 to 0.4% of (methylhydrogen]silylene]] (n≈60) (CAS No. 207 574-74-1, for example Parsol SLX),
    2,2'-methylenebis(6-(2H-benzotriazol-2-yl)-4-(1,1,3,3-tetramethylbutyl)-phenol) (CAS No. 103 597-45-1, for example Tinosorb M),
    2,4-bis{[4-(2-ethylhexyloxy)-2-hydroxy]phenyl}-6-(4-methoxyphenyl)-1,3,5-triazine (CAS No. 187 393-00-6, foe example Tinosorb S),
    hexyl 2-(4-diethylamino-2-hydroxybenzoyl)benzoate (for example Uvinul® UVA Plus).

The compounds listed should only be regarded as examples. It is of course also possible to use other UV filters. These organic UV filters, like the compounds of the formula I, are generally incorporated into the cosmetic formulations according to the invention in an amount of from 0.5 to 20% by weight, preferably in an amount of from 1 to 15% by weight and particularly preferably in amounts of from 2 to 8% by weight per individual substance. In total, the cosmetic formulations according to the invention usually comprise up to 40% by weight, preferably from 5 to 25% by weight, of organic UV filters of this type.

Conceivable inorganic UV filters are those from the group consisting of titanium dioxides, such as, for example, coated titanium dioxide (for example Eusolex® T-2000, Eusolex® T-AQUA), zinc oxides (for example Sachtotec®), iron oxides and also cerium oxides. These inorganic UV filters are generally incorporated into the cosmetic formulations according to the invention in an amount of from 0.5 to 20% by weight, preferably from 2 to 10% by weight.

If different inorganic or organic UV filters are employed, these can be used in virtually any desired ratios to one another. The ratios of the individual substances to one another are usually in the range 1:10-10:1, preferably in the range 1:5-5:1 and particularly preferably in the range 1:2-2:1. If UV-A filters are employed alongside UV-B filters, it is advantageous for most applications for the proportion of UV-B filters to predominate and the ratio of UV-A filters: UV-B filters to be in the range from 1:1 to 1:10.

Preferred compounds having UV-filtering properties which are used in the cosmetic formulations according to the invention are 3-(4'-methyl-benzylidene)-dl-camphor, 1-(4-tert-butylphenyl)-3-(4-methoxyphenyl)propane-1,3-dione, 4-isopropyldibenzoylmethane, 2-hydroxy-4-methoxy-benzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate and coated titanium dioxide.

The cosmetic formulation according to the invention may also—apart from the compounds of the formulae Ia and Ib—comprise one or more amino acids or pharmaceutically tolerated salts thereof. Preferred amino acids are selected from the group of compounds consisting of alanine, valine, leucine, isoleucine, proline, methionine, phenylalanine, tryptophan, glycine, serine, threonine, cysteine, tyrosine, asparagine, glutamine, lysine, arginine and histidine.

If the formulation according to the invention comprises amino acids which are different from the compounds of the formulae Ia and Ib, the proportion of these amino acids or pharmaceutically tolerated salts thereof in the cosmetic formulation according to the invention is preferably from 0.1 to 10% by weight, particularly preferably from 0.1 to 8% by weight and especially preferably from 0.2 to 5% by weight, based on the formulation as a whole. The proportion of these amino acids or pharmaceutically tolerated salts thereof in the cosmetic formulation according to the invention is very especially preferably from 0.2 to 2% by weight, based on the formulation as a whole.

If the formulation according to the invention comprises amino acids which are different from the compounds of the formulae Ia and Ib, the pH of the formulation is preferably less than 4.

The ingredients may be incorporated into the cosmetic formulations according to the invention in a conventional manner. Formulations are suitable for external application, for example as a cream, lotion or gel, or as a solution which can be sprayed onto the skin. It is preferred here for the formulation to comprise at least one oil phase and at least one water phase.

Application forms of the cosmetic formulations according to the invention which may be mentioned are, for example: solutions, emulsions, PIT emulsions, suspensions, ointments, gels, creams, lotions, sprays and aerosols. Further application forms are, for example, sticks. Any desired conventional vehicles, assistants and optionally further active ingredients may be added to the formulation.

Preferred assistants originate from the group consisting of preservatives, antioxidants, stabilisers, solubilisers, vitamins, colorants, odour improvers, film formers, thickeners and humectants.

Solutions and emulsions can comprise the conventional vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize oil, olive oil, castor oil and sesame oil, glycerol fatty acid esters, polyethylene glycols and fatty acid esters of sorbitan, or mixtures of these substances.

The emulsions may exist in various forms. Thus, they can be, for example, an emulsion or microemulsion of the water-in-oil (W/O) type or of the oil-in-water (O/W) type, or a multiple emulsion, for example of the water-in-oil-in-water (W/O/W) type.

The cosmetic formulations according to the invention may also be in the form of emulsifier-free, disperse preparations. They can be, for example, hydrodispersions or Pickering emulsions.

Suspensions may comprise conventional vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams may comprise conventional vehicles, for example animal and vegetable fats, waxes, paraffins, starch, traga-canth, cellulose derivatives, polyethylene glycols, silicones, bentonites, silicic acid, talc and zinc oxide, or mixtures of these substances.

Face and body oils may comprise the conventional vehicles, such as synthetic oils, such as fatty acid esters, fatty alcohols, silicone oils, natural oils, such as vegetable oils and oily plant extracts, paraffin oils, lanolin oils, or mixtures of these substances.

Sprays may comprise the conventional propellants, for example chlorofluorocarbons, propane/butane or dimethyl ether.

Further typical cosmetic application forms are, for example, make-up, such as, for example, emulsion make-up, and sun-protection, pre-sun and after-sun preparations.

The cosmetic formulation according to the invention is particularly suitable for protecting human skin against the harmful effects of the UV components in sunlight and in addition it also offers protection against ageing processes in the skin and against oxidative stress, i.e. against damage caused by free radicals, as are produced, for example, by solar radiation, heat or other influences. In this connection, it is in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a cream or milk which comprises fatty alcohols, fatty acids, fatty acid esters, in particular triglycerides of fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic formulation according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, the conventional propellants, such as alkanes, fluoroalkanes and chlorofluoroalkanes, are generally used.

For protection of the skin against sunlight, a cosmetic formulation according to the invention is applied to the skin.

Even without further comments, it is assumed that a person skilled in the art will be able to utilise the above description in its broadest scope. The preferred embodiments should therefore merely be regarded as descriptive disclosure which is absolutely not to be regarded as limiting in any way.

The complete disclosure content of all applications and publications mentioned above and below is incorporated into this application by way of reference.

The cosmetic formulations according to the invention can be prepared with the aid of techniques which are well known to the person skilled in the art.

All compounds or components which can be used in the cosmetic formulations according to the invention are either known and commercially available or can be obtained or prepared by methods which are well known to the person skilled in the art and are described in the literature (for example in standard works, such as Houben-Weyl, Methoden der organischen Chemie [Methods of Organic Chemistry], Georg-Thieme-Verlag, Stuttgart).

The following examples are intended to illustrate the present invention. However, they should absolutely not be regarded as limiting.

The INCI names of the raw materials used are as follows:

| Raw material | INCI name |
|---|---|
| Cetiol | Oleyl Oleate |
| Dihydroxyacetone | Dihydroxyacetone |
| Dow Corning 3225 C | Cyclomethicone, Dimethicone Copolyol |
| Emulsifier E 2155 | Steareth-10, Steareth-7, Stearyl Alcohol |
| Imwitor 900 | Glyceryl Stearate |
| Luvitol EHO | Cetearyl Octanoate |
| Methyl 4-hydroxybenzoate | Methylparaben |
| Miglyol 812 N | Caprylic/Capric Triglyceride |
| Paracera M | Microwax |
| Propane-1,2-diol | Propylene Glycol |

-continued

| Raw material | INCI name |
|---|---|
| Propyl 4-hydroxybenzoate | Propylparaben |
| RonaCare ™ ectoin | Ectoin |
| Tegin Acid H | Glyceryl Stearate, Ceteth-20 |
| Water, demineralised | Aqua (Water) |

EXAMPLES

Example 1

Self-tanning lotion (O/W)

| | | | % by wt. |
|---|---|---|---|
| A | Emulsifier E 2155 | (1) | 3.0 |
| | Tegin Acid H | (1) | 3.0 |
| | Imwitor 900 | (2) | 3.0 |
| | Paracera M | (3) | 1.0 |
| | Cetiol | (4) | 8.5 |
| | Luvitol EHO | (5) | 11.5 |
| | Miglyol 812 N | (6) | 8.5 |
| | Propyl 4-hydroxybenzoate | (7) | 0.05 |
| B | Propane-1,2-diol | (7) | 4.0 |
| | Water, demineralised | | 42.2 |
| | Methyl 4-hydroxybenzoate | (7) | 0.15 |
| C | Dihydroxyacetone | (7) | 5.0 |
| | RonaCare ™ ectoin | (1) | 0.1 |
| | Water, demineralised | | 10.0 |

Preparation

Phase A is heated to 75° C. and phase B to 80° C. Phase B is subsequently added slowly to phase A with stirring and homogenised. At about 40° C., phase C is added and allowed to cool with stirring.

| Sources of supply | |
|---|---|
| (1) | Th. Goldschmidt AG |
| (2) | Huls AG |
| (3) | Paramelt |
| (4) | Cognis GmbH |
| (5) | BASF AG |
| (6) | Condea Chemie GmbH |
| (7) | Merck KGaA |

Example 2

Self-tanning milk (W/O)

| | | | % by wt. |
|---|---|---|---|
| A | Dow Corning 3225 C | (2) | 23.6 |
| B | Dihydroxyacetone | (1) | 5.0 |
| | Propane-1,2-diol | (1) | 35.9 |
| | Preservatives | | q.s. |
| | RonaCare ™ ectoin | (1) | 1.0 |
| | Water, demineralised | | to 100 |

Preparation

Phase B is dissolved and subsequently stirred into phase A.

The preservatives used are the following:
0.05% of propyl 4-hydroxybenzoate
0.15% of methyl 4-hydroxybenzoate

| Sources of supply | |
|---|---|
| (1) | Merck KGaA |
| (2) | Dow Corning |

The invention claimed is:

1. A cosmetic composition comprising dihydroxyacetone, a topical vehicle, and a compound of formula Ia or Ib, or a pharmaceutically acceptable salt of a compound of formula Ia or Ib

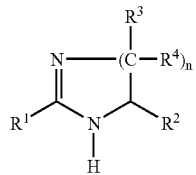

Ia

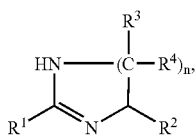

Ib wherein
$R^1$ is H or alkyl,
$R^2$ is H, COOH, COO-alkyl or CO—NH—$R^5$,
$R^3$ and $R^4$ are each, independently of one another, H or OH,
n is 1, 2 or 3,
alkyl is an alkyl radical having 1 to 4 carbon atoms, and
$R^5$ is H, alkyl, an amino acid radical, a dipeptide radical or a tripeptide radical.

2. A cosmetic composition according to claim 1, which contains 0.1 to 15% by weight of dihydroxyacetone based on the formulation as a whole.

3. A cosmetic composition according to claim 1, which contain 0.001 to 50% by weight of a compound of formula Ia or Ib, or a pharmaceutically acceptable salt of a compound of formula Ia or Ib based on the formulation as a whole.

4. A cosmetic composition according to claim 1, wherein the compound of formula Ia or Ib is (S)-1,4,5,6-tetrahydro-2-methyl4-pyrimidinecarboxylic acid and (S,S)-1,4,5,6-tetrahydro-5-hydroxy-2-methyl-4-pyrimidinecarboxylic acid.

5. A cosmetic composition according to claim 1, further comprising one or more antioxidants.

6. A cosmetic composition according to claim 1, further comprising one or more UV filters.

7. A cosmetic composition according to claim 1, which is a composition used for self-tanning, for day care or light-protection.

8. A method for augmenting the UV-A-protective action of dihydroxyacetone comprising formulating a cosmetic composition of claim 1 which comprise bringing into said cosmetic dihydroxyacetone and a compound of formula Ia or Ib, or a pharmaceutically acceptable salt of a compound of formula Ia or Ib.

9. A cosmetic composition according to claim 1, which contains a stereoisomeric form of a compound of formula Ia or Ib.

10. A cosmetic composition according to claim 7, which is a composition used for light-protection.

* * * * *

UNITED STATES PATENT AND TRADEMARK OFFICE
CERTIFICATE OF CORRECTION

PATENT NO. : 7,311,895 B2
APPLICATION NO. : 10/485389
DATED : December 25, 2007
INVENTOR(S) : Sabine Hitzel It is certified that error appears in the above-identified patent and that said Letters Patent is hereby corrected as shown below:

Column 14, line 19 reads "acid and (S,S)" should read -- acid or (S,S) --
Column 14, line 30 reads "which comprise" should read -- which comprises --

Signed and Sealed this

Seventeenth Day of June, 2008

JON W. DUDAS
*Director of the United States Patent and Trademark Office*